(12) United States Patent
Blum

(10) Patent No.: US 9,855,062 B2
(45) Date of Patent: *Jan. 2, 2018

(54) TOTAL KNEE PROSTHESIS AND METHOD FOR TOTAL KNEE ARTHROPLASTY

(76) Inventor: Michael F. Blum, Birmingham, AL (US)

( * ) Notice: Subject to any disclaimer, the term of this patent is extended or adjusted under 35 U.S.C. 154(b) by 1155 days.

This patent is subject to a terminal disclaimer.

(21) Appl. No.: 12/413,099

(22) Filed: Mar. 27, 2009

(65) Prior Publication Data
US 2009/0306784 A1 Dec. 10, 2009

Related U.S. Application Data

(63) Continuation of application No. 12/134,713, filed on Jun. 6, 2008, now Pat. No. 7,998,203.

(51) Int. Cl.
*A61F 2/38* (2006.01)
*A61B 17/17* (2006.01)
*A61F 2/30* (2006.01)

(52) U.S. Cl.
CPC ...... *A61B 17/1714* (2013.01); *A61B 17/1764* (2013.01); *A61F 2/38* (2013.01); *A61F 2/3836* (2013.01); *A61F 2002/30604* (2013.01)

(58) Field of Classification Search
USPC .......... 623/13.11–13.2, 20.24, 20.25, 20.28, 623/20.3, 20.31
See application file for complete search history.

(56) References Cited

U.S. PATENT DOCUMENTS

| | | | |
|---|---|---|---|
| 4,770,663 A * | 9/1988 | Hanslik et al. | 623/13.12 |
| 6,267,767 B1 | 7/2001 | Strobel et al. | |
| 6,482,210 B1 * | 11/2002 | Skiba et al. | 606/86 R |
| 6,905,513 B1 | 6/2005 | Mtezger | |
| 2005/0187635 A1 * | 8/2005 | Metzger | 623/20.15 |

* cited by examiner

*Primary Examiner* — Bruce E Snow
(74) *Attorney, Agent, or Firm* — The Gache Law Firm, P.C.; Russell C. Gache

(57) ABSTRACT

A prosthetic knee implant for implantation into a mammal, which accommodates an anterior cruciate ligament substitute to provide stability to the knee implant. The prosthetic knee implant includes a femoral component having a pair of condylar surfaces and a tibial component having a surface portion adapted to slidably engage the femoral component upon rotation of the same. The femoral component further includes a central femoral recess between the condyles providing access to the femur for drilling a channel through which a cruciate ligament substitute may be integrated into the femur. The tibial component further includes a center portion defining an aperture through which the ligament substitute maybe threaded through the tibia and integrated therein, or anchored upon its surface. Also disclosed is a method used to replace the total knee joint in a mammal with the improved prosthetic knee implant of the present invention.

29 Claims, 7 Drawing Sheets

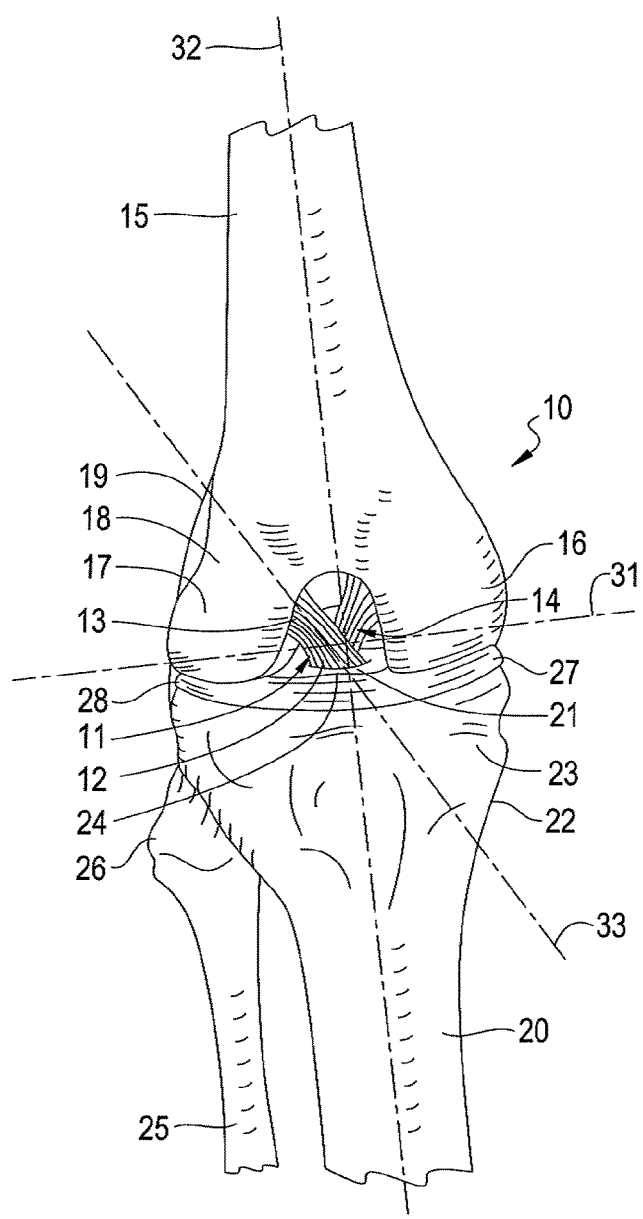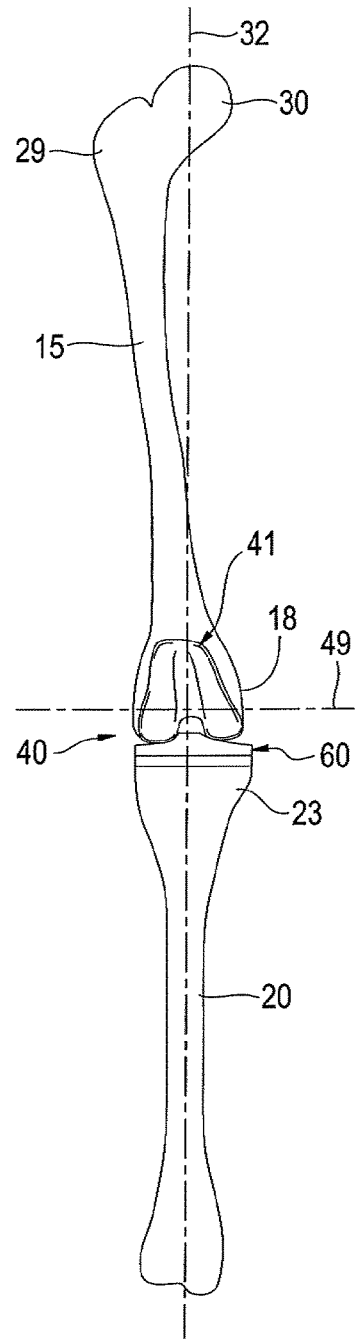
FIG. 1
FIG. 2

TOTAL KNEE PROSTHESIS AND METHOD FOR TOTAL KNEE ARTHROPLASTY

This application claims the benefit of filing priority under 35 U.S.C. §119 and 37 C.F.R. §1.78 from U.S. Nonprovisional application Ser. No. 12/134,713 filed Jun. 6, 2008, for a Total Knee Prosthesis and Method for Total Knee Arthroplasty. All information disclosed in the prior application is incorporated herein by reference

FIELD OF INVENTION

The present invention relates generally to prosthetic knee implants and corresponding surgical methods used to replace the total knee joint in a mammal. More particularly, the invention relates to a prosthetic knee implant having a femoral component and a tibial component, which are adapted to receive an anterior cruciate ligament substitute for biasing the femur and tibia together.

BACKGROUND OF INVENTION

Mammalian knees wear out for a variety of reasons, including inflammation from arthritis, injury, or simple wear and tear. Over the past 40 years, total knee arthroplasties (commonly referred to as total knee replacements or "TKR") have become the standard of care for end-stage arthritis. In most TKR procedures, the natural bearing surfaces of the upper portion of the tibia (tibial plateau) and the lower portion of the femur (femoral condyles) are resected and replaced with artificial material. Specifically, approximately between 0.5 to 1.5 centimeters of the upper portion of the tibia, including both the intercondylar eminence and the medial and lateral tibial plateaus, are resected, leaving a relatively flat surface onto which a rigid support member is affixed. Then, a synthetic surface portion is affixed to the support member, with the surface portion simulating the intercondylar eminence and the tibial plateaus. A lower end portion of the femur is then resected, and a member having bearing surfaces replicating the femoral condyles is then affixed to the remaining end of the femur.

The majority of currently available prosthetic knee implants employed for TKR do not retain the natural anterior cruciate ligament. Rather, during the implant procedure, the anterior cruciate ligament is either removed or, if preservation is attempted, has been found to rupture shortly after implant of the prosthesis. This is particularly true for TKR candidates, who often have a sacrificed anterior cruciate ligament going into the surgery. As a result, the mechanical interaction between the femoral and tibial components in a TKR is the primary means to stabilize the anterior-posterior motion of the knee.

Although the existing TKR prostheses succeed in increasing patient mobility, and provide the patient with the desired therapeutic result, at least one significant disadvantage remains. Namely, in a TKR wherein the anterior cruciate ligament is lacking, the femoral condyles translate in a posterior direction in full extension and translate in an anterior direction in flexion, which is reverse of the motions in a natural knee joint. Such abnormal translation and pivot shift often results in the patient's compromised functional abilities, such as quadriceps avoidance, and changed upper body mechanics during activities such as stair climbing and rising from a chair. Even asymptomatic patients show gait abnormalities that could lead to reduced functional ability to perform activities of daily living over time.

Further, abnormal anterior translation of the TKR can lead to accelerated wear of the prosthesis. Indeed, current TKR prostheses have a functional lifespan of approximately 15 years, such that younger patients (who are increasingly receiving TKRs) are more likely to require revision surgery as they age. The amount of bone loss that is inherent in a TKR makes a revision procedure much more difficult in the future as even more bone must be removed.

Existing TKR prostheses attempt to compensate for the loss of the anterior cruciate ligament by containing or limiting the amount of abnormal translation in the nonstabilized knee. For example, U.S. Pat. No. 5,413,604 discloses a TKR prosthesis wherein the anterior cruciate ligament must be sacrificed, thereby resulting in a nonstabilized TKR with abnormal anterior translation. Without an anterior cruciate ligament, the prosthesis relies primarily on the mechanical interaction between the femoral and tibial components as a means to accommodate the abnormal anterior translation and stabilize the knee. Similarly, U.S. Pat. No. 7,014,660 discloses a TKR prosthesis that incorporates a control arm and stop pin assembly to limit the amount of anterior sliding movement caused by the lack of the anterior cruciate ligament. Unfortunately, neither prosthesis disclosed in the '604 and '660 patents actually prevents the abnormal anterior translation of the nonstabilized TKR; or as shown in recent medical research pertaining to medial and lateral translation of ACL deficient knees, rather, they only attempt to accommodate or limit it. As a result, the patient's functional abilities remain limited, and the prosthesis is subject to premature wear and tear. The U.S. Pat. Nos. 5,413,604 and 7,014,660 are hereby incorporated by reference in their entireties.

Therefore, there exists a constant need in this art for an improved TKR prosthesis that allows for the replacement of an anterior cruciate ligament, and approaches the mobility, stability and longevity of a natural, healthy knee joint.

SUMMARY OF THE INVENTION

The present invention is directed to a prosthetic knee implant, and more particularly, to a prosthetic knee implant having a femoral component including a medial and lateral condyle, and a tibial component including a surface portion adapted to slidably engage the femoral component upon rotation of the same. The femoral component includes diverging curved members extending downward and placed on or near the medial and lateral condyles. These members define a recess in the lower central portion of the femoral component. The tibial component includes a center portion defining an aperture through the tibial component substantially at its center. The central femoral recess and the tibial aperture are adapted to receive an anterior cruciate ligament substitute for biasing the femur and the tibia together.

In addition, a method of total knee joint replacement in a mammal is presented consisting of replacing at least a portion of the lower femur with the improved prosthetic femoral component; replacing at least a portion of the upper tibia with the improved prosthetic tibial component; engaging a drill alignment guide to the femur between the femoral condyles and drilling a longitudinal channel through the central femoral recess and into the femur; engaging a drill alignment guide to the tibial component and extending the tibial aperture by drilling a longitudinal channel through the tibia aperture and into the tibia. The method further includes threading an anterior cruciate ligament substitute into the femoral channel and into the tibial channel and anchoring a first end of the ligament substitute to bone leaving a free end;

applying tension to the free end; and, anchoring the free end to bone under tension such that said femur and the tibia are biased together.

BRIEF DESCRIPTION OF THE DRAWINGS

A total knee prosthesis apparatus and a method for total knee replacement incorporating the features of the invention are depicted in the attached drawings which form a portion of the disclosure and wherein:

FIG. 1 is an anatomical view of a human knee joint having an anterior cruciate ligament and posterior cruciate ligament;

FIG. 2 is a diagram of a prosthetic knee implant in accordance with a preferred embodiment of the present invention, and implanted at the joint between a human femur and tibia to provide a total knee replacement;

DESCRIPTION OF THE PREFERRED EMBODIMENTS

Figure 3:
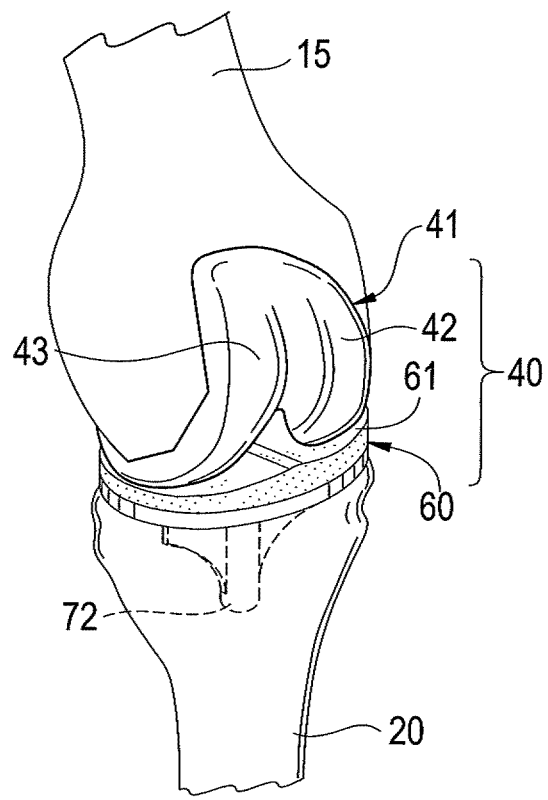
FIG. 3 is a perspective view of the prosthetic knee implant of FIG. 2.

Referring to the drawings for a better understanding of the function and structure of the invention, FIG. 1 shows a typical patient's natural knee joint 10 prior to the surgical procedure. Illustrated is upper portion 23 of the tibia 20 the upper portion 26 of the fibula 25, the lower portion 18 of the femur 15, the exterior surface 19 of the femur 15, as well as the medial condyle 16 and lateral condyle 17. The anterior cruciate ligament 11 and the posterior cruciate ligament 14 are seen to be present in the knee joint 10. One end 12 of the anterior cruciate ligament 11 is attached to the anterior portion of the intercondylar eminence 21 of the tibia 20, and the second end 13 of the anterior cruciate ligament 11 is attached to the posterior portion of the medial aspect of the lateral femoral condyle 17, thereby defining an axis 33 of the anterior cruciate ligament 11. The posterior cruciate ligament 14 passes upward and forward on the medial side of the anterior cruciate ligament 11, extending from behind the intercondylar eminence 21 to the lateral side of the medial condyle 16 of the femur 15. Also seen is the exterior surface 22 of the tibia 20, the tibial plateau 24, the medial meniscal cartilage 27 and lateral meniscal cartilage 28.

The femur 15 and tibia 20 extend along a mechanical axis 32 which is generally parallel to the tibia 20 and passes through the head 30 of the natural hip joint (not shown). The tibia 20 rotates about an axis 31 relative to the lower portion 18 of the femur 15 that bisects the condyles 16 and 17 and is generally perpendicular to the mechanical axis 32. Axis 31 corresponds with what is referred to in the medical industry as the "knee joint line," this joint line being separated into a medial joint line portion which is the portion of the joint line starting at the intersection of the axis 32 and axis 31 and extending to the right (i.e. in the medial direction) of the knee joint, and a lateral joint line which is the portion of the line starting at the intersection of the axis 32 and axis 31 and extending to the left (i.e. in the lateral direction) of the knee joint. During articulation of the knee joint 10 between flexion and extension, the medial condyle 16 engages the tibia 20 along a medial bearing surface bordered by the medial meniscal cartilage 27, while the lateral condyle 17 engages the tibia 20 along a lateral bearing surface bordered by the lateral meniscal cartilage 28. The anterior crucial ligament 11 limits forward movement of the tibia 20 under the femoral condyles 16 and 17, while the posterior cruciate ligament 14 limits backward movement of the tibia 20 under the femoral condyles 16 and 17.

Referring now to FIG. 2, the natural knee joint 10 has been replaced by a prosthetic knee implant 40 constructed in accordance with a preferred embodiment of the present invention. The prosthetic knee implant 40 includes a femoral component 41 affixed to the lower portion 18 of the femur 15 and a tibial component 60 affixed to the upper portion 23 of the tibia 20. The femoral component 41 includes a tibial axis of rotation 49 relative to the lower portion 18 of the femur 15 that is generally perpendicular to the mechanical axis 32 and is also oriented in substantial similarity to axis 31 of FIG. 1.

Figure 4:
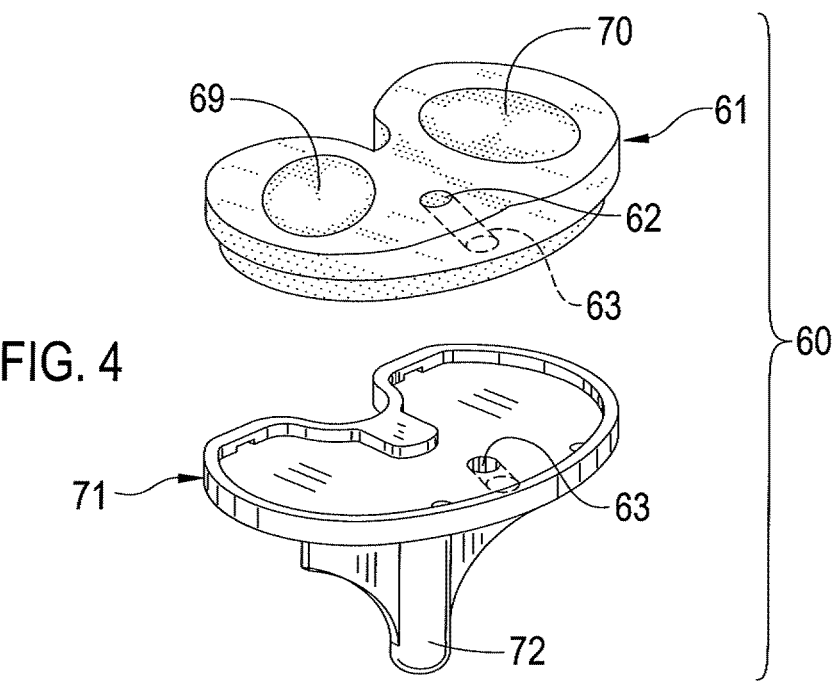
FIG. 4 is an exploded perspective view of the tibial component.

Referring to FIGS. 3 and 4, the femoral component 41 includes a replacement medial condyle 42 and a replacement lateral condyle 43 of the femur 15. Normally, the ends of the femoral condyles 16 and 17 are resected and shaped to receive the femoral component 41 and affixed to the femur 15 as is known in the art, such as adhesion using bone cement and/or pegs extending into the condyles 16 and 17.

The tibial component 60 includes a surface portion 61 adapted to slidably engage the femoral component 41 upon rotation of the tibia 20 about tibial axis 49, in such a manner as to enable the prosthetic knee implant 40 to serve as a substitute for the natural knee joint 10 for relative motion of the femur 15 and tibia 20 between flexion and extension. In a preferred embodiment, the tibial component 60 provides replacement bearing surfaces in the form of lateral bearing surface 69 for engagement by the lateral condyle 43 and medial bearing surface 70 for engagement by the medial condyle 42 of the prosthetic knee implant 40. The tibial component 60 further includes a center portion 62 that defines an aperture 63 through the tibial component 60 substantially at its center. Preferably, the tibial aperture 63 is of sufficient size to accommodate a replacement anterior cruciate ligament.

Typically, the natural anterior cruciate ligament 11 is removed, along with approximately between 0.5 to 1.5 centimeters of the upper portion 23 of the tibia 20, including the tibial plateau 24, the intercondylar eminence 21, the medial meniscal cartilage 27, and the lateral meniscal cartilage 28, thereby leaving a relatively flat surface onto which the tibial component 60 is affixed. In a preferred embodiment, the tibial component 60 includes a support member in the form of a platform 71 having a unitary depending stem 72 inserted into the tibia 20 to assist in the accurate location and affixation of the platform 71 on the tibia 20. In a preferred embodiment, a surface portion 61 is secured in place on platform 71 to be interposed between the femoral component 41 and platform 71 for providing medial and lateral bearing surfaces 70 and 69 and for engagement by the medial condyle 42 and the lateral condyle 43, respectively, to enable articulation of the prosthetic knee implant 40. The condyles 42 and 43 preferably are constructed of a biocompatible high-strength alloy, while the preferred material for the surface portion 61 is a synthetic polymeric material, such as high-density polyethylene. Surface portion 61 may be secured in place on platform 71 by means of any of several securing arrangements as described in greater detail in U.S. Pat. No. 5,413,604.

In effecting implant of the prosthetic implant 40, the anterior cruciate ligament 11 of the natural knee has been sacrificed. Thus, during articulation of the prosthetic implant 40 between flexion and extension the condyles 42 and 43 translate in a posterior direction in full extension and translate in an anterior direction in flexion, as described in greater detail in U.S. Pat. No. 5,413,604, col. 4, lines 41-67.

Figure 5:
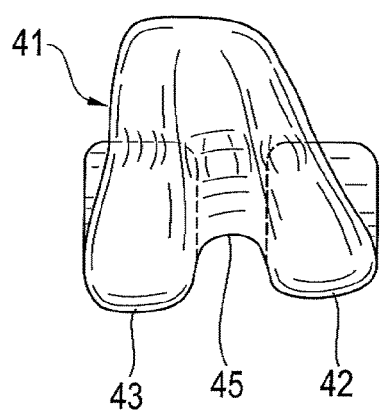
FIG. 5 is a partial exploded view of the femoral component.

Referring to FIG. 5, the femoral component 41 includes the two diverging curved medial and lateral condyle members 42,43 that extend downward and define a recess 45 in the lower central portion of the femoral component. The central femoral recess 45 provides access to the femur 15 between the medial and lateral condyles 16 and 17, now resected in favor of implant condyles 42 and 43. Preferably, the central femoral recess 45 is of sufficient size to accommodate the integration of an anterior cruciate ligament substitute through a channel in the femur, as will be described.

Figure 6A:
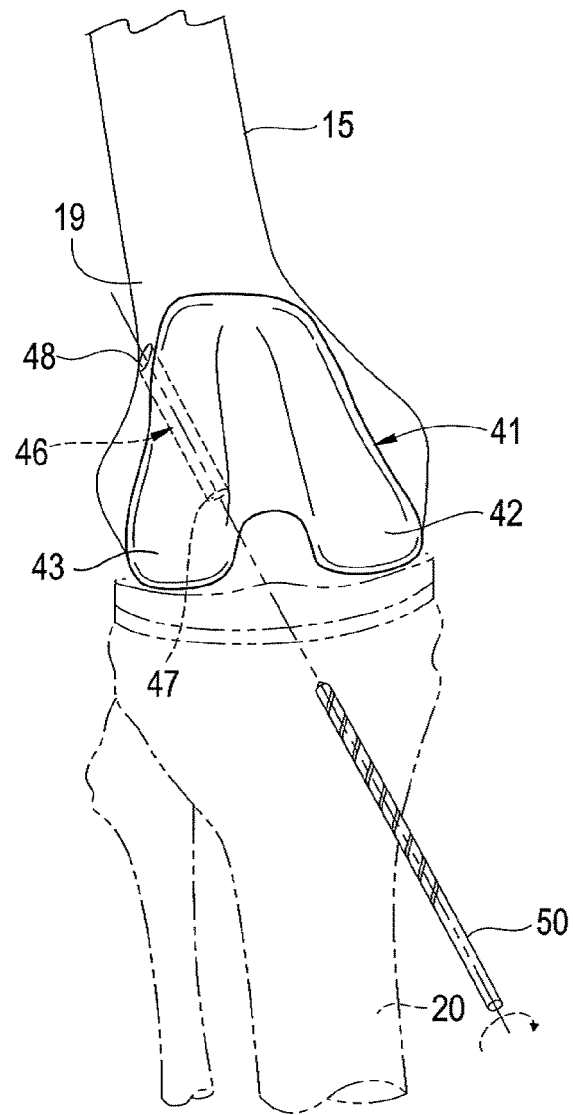
FIG. 6A is an illustration of the femur of FIG. 2 having the femoral channel drilled longitudinally through the central femoral recess and into the femur.

Referring to FIG. 6A, a longitudinal channel 46 is drilled in a conventional manner through the central femoral recess 45 and into the femur 15. In a preferred embodiment, the femoral channel 46 has lower opening 47 and upper opening 48. Alternatively, femoral channel 46 does not extend through the exterior surface 19 of the femur 15 but terminates within the femur 15 bone where it is implanted. The femoral channel 46 is drilled using a conventional two-step process with the engagement of a drill guide (depicted in FIG. 6B) to the femoral component 41 between the femoral condyles 42 and 43 in the central femoral recess 45, followed by a drill 50 to create the femoral channel 46 of sufficient size to accommodate an anterior cruciate replacement. In a preferred embodiment, the drill guide (depicted in FIG. 6B) is configured to align the femoral channel 46 with the tibial aperture 66, as will be discussed. The femoral channel 46 is typically debrided of all surrounding debris at upper opening 48, and any sharp edges are chamfered using a conventional bone rasp or reamer.

Figure 6B:
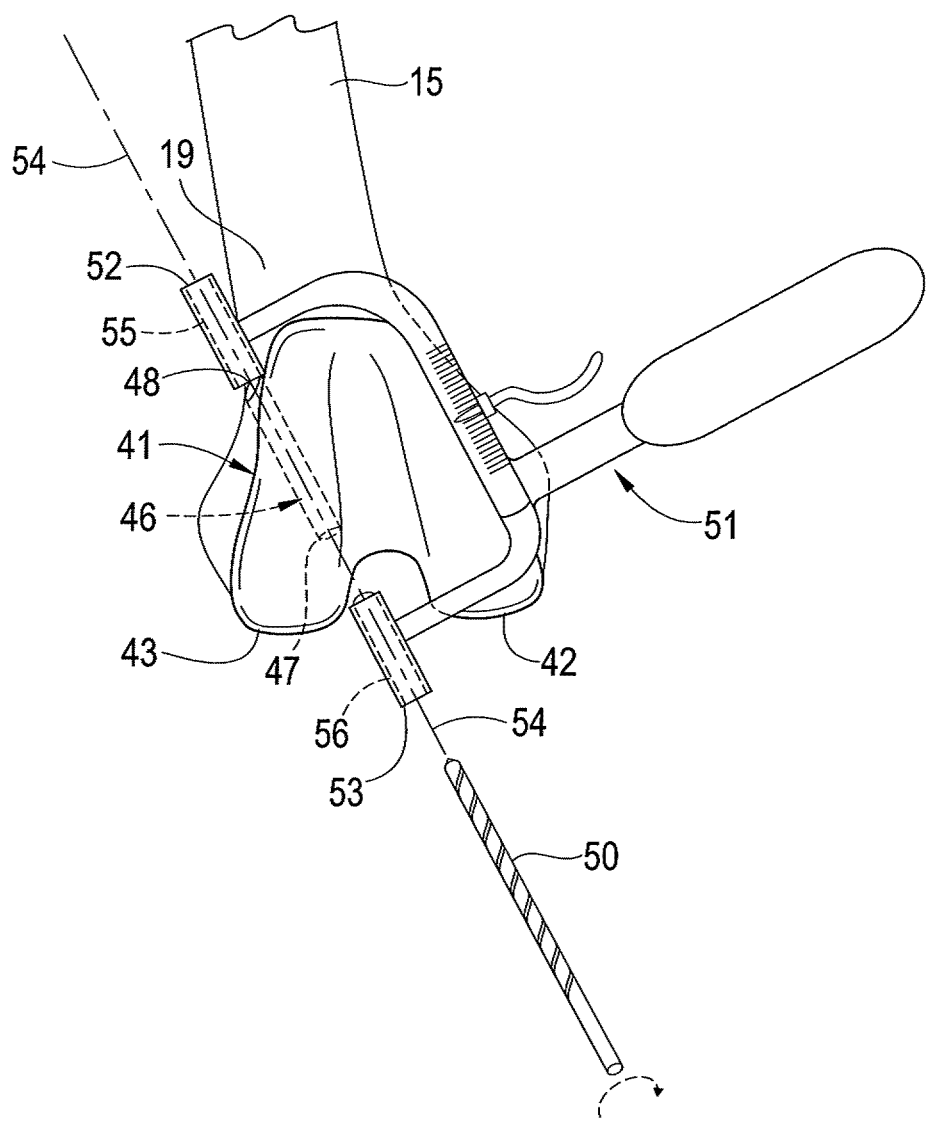
FIG. 6B is an illustration of the femur of FIG. 2 with an aligned drill guide for drilling longitudinally through the central femoral recess and into the femur.

Referring to FIG. 6B, there is shown a drill guide 51 engaged adjacent to the femoral component 41 to provide a temporary guide for the drill 50 while drilling the femoral channel 46 through central femoral recess 45. In a preferred embodiment, the guide 51 includes a first sleeve 52 and a second sleeve 53 aligned longitudinally along a drilling axis 54. The first sleeve 52 and second sleeve 53 each include an aperture 55 and 56 disposed longitudinally along the drilling axis 54 suitable for allowing the passage of a drill bit 50.

Figure 7:
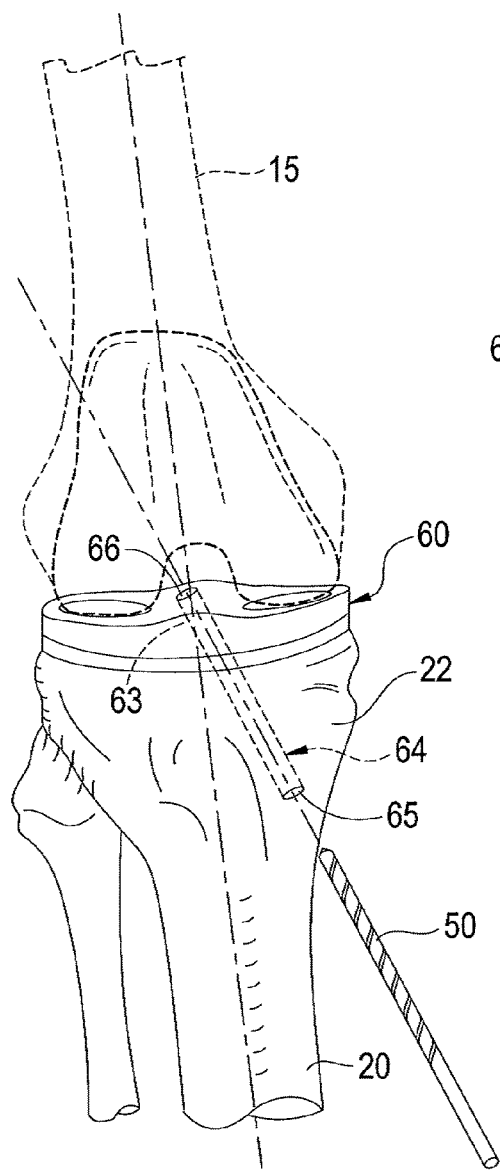
FIG. 7 is an illustration of the tibia of FIG. 2 having the tibial channel drilled longitudinally through the tibial aperture and into the tibia.

Referring to FIG. 7, a longitudinal channel 64 is drilled in a conventional manner into the tibia 20 and through the tibial aperture 63. In a preferred embodiment, the tibial channel 64 has lower opening 65 and upper opening 66. Alternatively, tibial channel 64 does not extend through the exterior surface 22 of the tibia 20 but terminates within the tibia 20 bone and to which it is anchored. The tibial channel 64 is drilled using a conventional two-step process with the engagement of a drill guide 51 (FIG. 6B) to the tibial component 60, followed by a subsequent drill 50 to create the tibial channel 64 of sufficient size to accommodate an anterior cruciate ligament substitute. The tibial channel 64 is typically debrided of all surrounding debris at lower opening 65, and any sharp edges are chamfered using a conventional bone rasp. In a preferred embodiment, the surface portion 61 is affixed to platform 71 after the drilling of the tibial channel 64 to prevent damage to the surface portion 61 during drilling. Preferably, the tibial channel 64 and the femoral channel 46 are in alignment and are oriented along an axis generally parallel to the axis 33 of an anatomic anterior cruciate ligament 11.

As mentioned above, the drill guide 51 (FIG. 6B) may also be engaged with the tibial component 60 to facilitate drilling of the tibial channel 64. Specifically, the second sleeve 53 may be adapted to nest in and mate with the tibial aperture 63 to define a drilling axis for the drill 50 while drilling the tibial channel 64. The tibial channel 64 may be drilled from the lower opening 65 to the upper opening 66, or vice versa.

Figure 8:
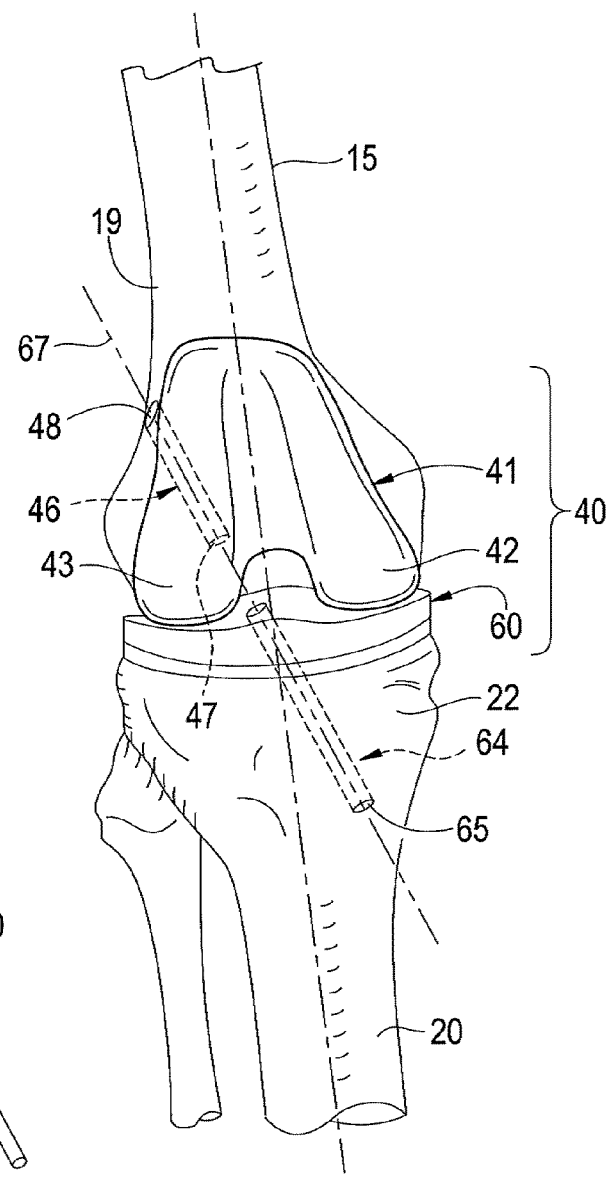
FIG. 8 is a combined illustration of FIG. 6A and FIG. 7, further depicting the femoral channel and tibial channel in substantial alignment in accordance with a preferred embodiment of the present invention.

Referring to FIG. 8, there is shown a prosthetic knee implant 40 constructed in accordance with a preferred embodiment. The femoral channel 46 extends through the exterior surface 19 of the femur 15 having lower opening 47 and upper opening 48. The tibial channel 64 extends through the exterior surface 22 of the tibia 20 having lower opening 65 and upper opening 66. Femoral channel 46 and tibial channel 64 are preferably in alignment and oriented along an axis 67 generally parallel to the axis 33 of a natural anterior cruciate ligament 11. The prosthetic implant 40 is now ready to have an anterior cruciate ligament substitute implanted.

The types of anterior cruciate ligament substitutes that can be used in the present invention include allografts, autografts, xenografts and synthetic grafts. Allografts include ligamentous tissue harvested from cadavers and appropriately treated, disinfected, and sterilized. Autografts consist of the patient's own ligamentous tissue harvested either from the patellar tendon or from the hamstring, or other substitute. Xenografts include ligamentous tissue harvested from one mammalian species and transplanted into or grafted onto another species, genus, or family (such as from porcupine to a human). Synthetic grafts include grafts made from synthetic polymers such as polyurethane, polyethylene, polyester and other conventional biocompatible, bioabsorbable or nonabsorbable polymers and composites.

Figure 9:
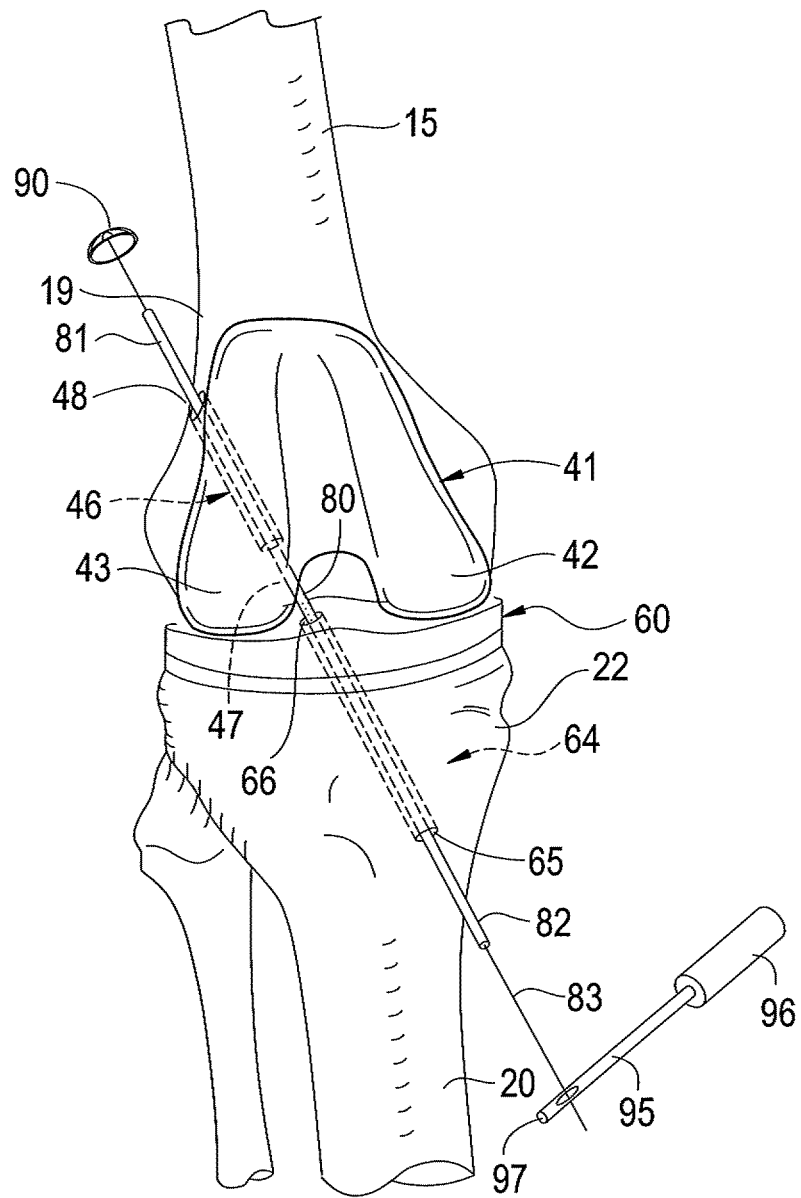
FIG. 9 illustrates the anterior cruciate ligament substitute with a self-anchoring umbrella-type anchor being threaded downward through the femoral channel and tibial channel.

Referring to FIG. 9, an anterior cruciate ligament substitute 80 is threaded down into the femoral channel 46 and the tibial channel 64. There are numerous methods and instruments known in the art that may be utilized to thread the anterior cruciate ligament substitute 80, which include the use of a suture passer (such as those disclosed in U.S. Pat. Nos. 5,746,754; 5,439,467; and 5,462,562), a graft-passing wire (such as that disclosed in U.S. Pat. No. 6,623,524), or a ligature carrier (such as that disclosed in U.S. Pat. No. 6,245,073 col. 2 lines 23-25) U.S. Pat. Nos. 5,746,754; 5,439,467; 5,462,562; 6,623,524; and 6,245,073 are hereby incorporated by reference in their entirety. Alternatively, the second end 82 of the ligament substitute 80 is passed down into the upper opening 48 of the femoral channel 46 until it exits the lower opening 47 of the femoral channel 46. A threading instrument 95 having a proximal handle 96 and a distal notched end 97 for engaging the ligament substitute 80 or a leading guide wire 83 attached to the ligament substitute 80 is provided. The distal end 97 of the threading instrument 95 is inserted into the lower opening 65 of the tibial channel 64 and is moved forward and out of the upper opening 66 of the tibial channel 64. Once the ligament substitute 80 is engaged in the distal notched end 97, the threading instrument 95 is withdrawn from the tibial channel 64, thereby pulling the guide wire 83 and passing the second end 82 of the ligament substitute 80 down through the upper opening 66 of the tibial channel 64 and out the lower opening 65 of the tibial channel 64. At that time, the guide wire 83 is removed from the threading instrument 95. The first end 81 of the ligament substitute 80 is anchored to the femur 15 using a conventional securing device such as cross-pins, femoral fasteners, endobuttons, screws, or staples. In a preferred embodiment, the first end 81 of the ligament substitute 80 is anchored to the exterior surface 19 of the femur 15 at the medial aspect of the posterior lateral femoral condyle with a self-anchoring umbrella anchor 90, as shown. Ideally, the ligament substitute 80 is coated with a substance that facilitates bone ingrowth into the ligament substitute 80, such as a hydroxyaptite (HA) coating. Then, the second end 82 of the ligament substitute 80 is placed in tension by the surgeon while the second end 82 is anchored to the bone of the tibia 20, thereby biasing the tibia 20 and femur 15 together. The second end 82 of the ligament substitute 80 may be anchored to the tibia 20 at the tibial anterior medial plateau, as shown, using a conventional securing device such as tibial fasteners, screws and washers, or staples. Alternatively, the ligament substitute 80 may be anchored from within the femur 15 and/or tibia 20 bone through use of a conventional securing device such as cross pins (such as those described in U.S. Pat. No. 7,032,599, col. 2, lines 42-62), screws, or anchors.

Figure 10:
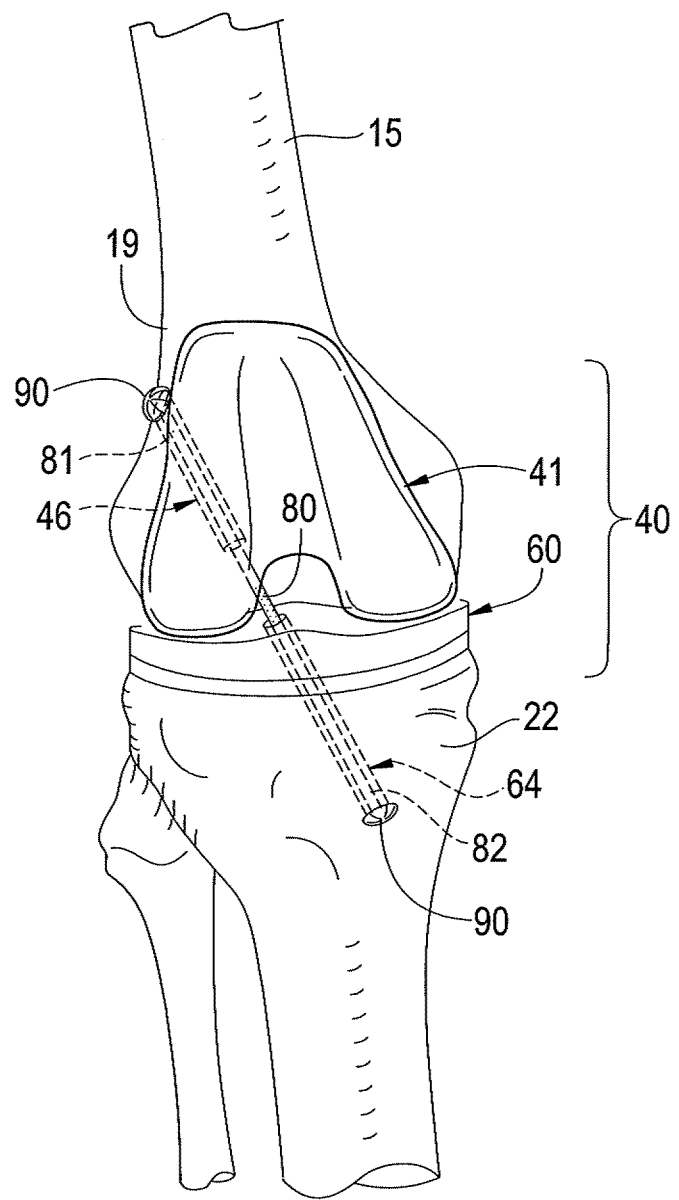
FIG. 10 illustrates the anterior cruciate ligament substitute threaded through the femoral and tibial channels, under tension, and anchored to the exterior surfaces of the femur and tibia with umbrella-type anchors.

Referring to FIG. 10, there is shown a prosthetic knee implant 40 constructed in accordance with a preferred embodiment. The first end 81 of the ligament substitute 80 is disposed longitudinally through the femoral channel 46 and anchored to the exterior surface 19 of the femur 15, and the second end 82 of the ligament substitute 80 is disposed longitudinally through the tibial channel 64 and anchored to the exterior surface 22 of the tibia 20 with a self-anchoring umbrella anchor 90. In the preferred embodiment, the ligament substitute 80 is oriented generally parallel to the axis 33 of the natural anterior cruciate ligament 11.

A surgical kit useful in practicing the method of total knee arthroplasty of the present invention is anticipated by the inventor. Such a kit would include the components previously described above. More specifically, the kit is seen to have a femoral component 41 including a replacement medial condyle 42 and a replacement lateral condyle 43, a tibial component 60 including a surface portion 61 adapted to slidably engage the femoral component 41 upon flexion and extension of the femoral component 41, an anterior cruciate ligament substitute 80, and means to anchor the ligament substitute 80 to the femur 15 and tibia 20, such as staples, screws or self-anchoring umbrella anchors 90. The tibial component 60 further includes a center portion 62 that defines an aperture 63 through the tibial component 60 substantially at its center. The kit would further include at least one drill guide component 51 cooperatively shaped to guide a drill bit through the central femoral recess 45 adjacent to the femur and through the aperture 63 of the tibial components 60.

As will be apparent to one skilled in the art, various modifications can be made within the scope of the aforesaid description. Such modifications being within the ability of one skilled in the art for a part of the present invention and are embraced by the claims below. For example, the inventor anticipates variations in the types of anchors used, the depth to which any ligament substitute end might be anchored inside bone, the degree and manner in which tension might be applied to a ligament substitute, and the placement of the apertures in the tibial components 61 and 71 for drilling. The priority in the steps of anchoring the ligament ends, whether above on the femur or below on the tibia, may be varied in accordance with the surgeon's experience and the particular operating situation is also anticipated.

Having set forth the nature of the invention, what is claimed is:

1. A prosthetic knee joint implant for replacing a knee joint and an associated anterior cruciate ligament of a mammal and for rotatably coupling a femur and tibia intersecting said knee joint together, comprising
   a. a femoral component for fixation to the lower portion of the femur, said femoral component including a medial and lateral condyle;
   b. a tibial component for fixation to the upper portion of the tibia, said tibial component including a surface portion adapted to slidably engage said femoral component upon rotation of said same;
   c. wherein said femoral component includes a recess between said medial and lateral condyles defining an access way into the femur;
   d. wherein said tibial component includes a bearing surface for cooperatively supporting said medial and lateral condyles, and wherein said bearing surface defines an aperture through the center of said bearing surface of said tibial component; and,
   wherein said femoral access way and said tibial aperture are aligned along an axis generally parallel to the axis of said associated anterior cruciate ligament and positioned to receive a ligament substitute extending along said axis.

2. A prosthetic implant as recited in claim 1, further comprising a ligament substitute having one end disposed longitudinally through said femoral access way and adapted to have one end anchored to said femur at the medial aspect of the posterior lateral femoral condyle, and having its other end adapted to be disposed longitudinally through said tibial component aperture for anchoring to the tibia.

3. A prosthetic implant as recited in claim 2, wherein said ligament substitute is adapted to have one end anchored to the tibial anterior medial plateau of the tibia.

4. A prosthetic implant as recited in claim 1, further comprising a ligament substitute, said ligament substitute adapted to cant laterally with respect to a vertical axis bisecting said knee joint and adapted to have at least a portion positioned adjacent to said access way and one end disposed through at least a portion of said lateral condyle.

5. A prosthetic implant as recited in claim 4, wherein said ligament substitute segment forms is adapted to form an angle with respect to a sagittal plane bisecting said knee joint approximating the angle made by said associated anterior cruciate ligament with respect to said sagittal plane.

6. A prosthetic implant as recited in claim 4, wherein said ligament substitute segment is adapted to be aligned along an axis generally parallel to the axis of said associated anterior cruciate ligament.

7. A prosthetic implant as recited in claim 1, wherein said tibial component includes no more than one aperture for passage of said ligament substitute through said tibial component and said tibial surface portion.

8. A prosthetic implant as recited in claim 7, wherein said bearing surface includes a raised portion at the center of said bearing surface through which said tibial aperture extends.

9. A prosthetic implant as recited in claim 8, wherein said tibial and femoral components are arranged relative to one another such that isometric movement occurs through the full range of motion of a natural mammalian knee joint.

10. The prosthetic implant of claim 1, further comprising an anterior cruciate ligament substitute, and wherein said ligament substitute comprises an axially aligned segment having an axis replicating an axis generally parallel to that of an anatomic anterior cruciate ligament.

11. The prosthetic implant of claim 1, further comprising an anterior cruciate ligament substitute and wherein said ligament substitute is canted laterally and traverses the interior of said lateral condyle and is confined within said femoral access way.

12. The prosthetic implant of claim 11, wherein one end of said ligament substitute is adapted to be positioned for anchoring to the tibial anterior medial plateau of the tibia.

13. The prosthetic implant of claim 1, further comprising a ligament substitute and wherein at least one end of said ligament substitute includes a self-anchoring umbrella type anchor.

14. The invention of claim 1, further comprising a ligament substitute and wherein one end of said ligament substitute is adapted to be positioned to extend through a bone and adapted to be anchored to the tibial anterior medial plateau of the tibia.

15. The prosthetic implant of claim 1, wherein one end of said ligament substitute is adapted to be positioned for anchoring to the medial aspect of the posterior lateral femoral condyle.

16. The prosthetic implant of claim 1, further comprising an anterior cruciate ligament substitute and wherein said ligament substitute is adapted to be non-parallel with respect to a sagittal plane bisecting said knee joint.

17. A prosthetic knee implant for replacing a knee joint and an associated anterior cruciate ligament connecting a mammalian femur and a mammalian tibia, comprising:
   a. means for replacing a lower portion of the mammalian femur, said femoral replacement means including means for replacing a medial and lateral condyle;
   b. means for replacing an upper portion of the mammalian tibia, said tibial replacement means including an upper surface;
   c. wherein said femoral replacement means includes a recess between said medial and lateral condyles means defining an access way into said femur;
   d. wherein said upper surface of said tibial replacement means further comprises a bearing surface for cooperatively supporting and slidably engaging said medial and lateral condyle means, and wherein said bearing surface defines an aperture through the center of said bearing surface of said tibial replacement means; and,
   e. wherein said femoral access way and said aperture in said tibial replacement means are aligned along an axis generally parallel to the axis of said associated anterior cruciate ligament and extending along said axis, wherein said access way is further adapted to define a tunnel in said femur, said tunnel adapted to cant laterally and have one end disposed adjacent to said access way and the other end disposed through said lateral condyle.

18. A prosthetic implant as recited in claim 17, further comprising a ligament substitute, and wherein said aperture is canted medially formed through said tibia replacement means and defines a passage way having an angle aligned with said axis such that said ligament substitute is adapted to be canted laterally with respect to a sagittal plane bisecting said knee joint.

19. A prosthetic implant as recited in claim 17, wherein said tibia replacement means includes not more than one aperture.

20. A prosthetic implant as recited in claim 17, further comprising a ligament substitute, and wherein one end of said ligament substitute is adapted to be positioned for anchoring to the tibial anterior medial plateau of the tibia and the other end is adapted to be positioned for anchoring to the medial aspect of the posterior lateral femoral condyle.

21. A method of replacing a knee joint in a mammal and for biasing a femur and tibia of the mammal together, comprising the steps of:
   a. replacing at least a portion of the lower femur with a prosthetic joint component, said femoral component including a medial and lateral condyle and further including a recess between said condyles defining an access way into the lower femur;
   b. replacing at least a portion of the upper tibia with a prosthetic joint component, said tibial component including a surface portion for receiving the surfaces of said femoral condyles and arranged for slidably supporting said same, said tibial component further including an aperture formed at its center;
   c. engaging a drill alignment guide to said femoral component between said medial and lateral condyles and drilling a longitudinal tunnel through the femur and intersecting the medial aspect of the posterior lateral femoral condyle;
   d. engaging a drill alignment guide to said tibial component and extending the femoral tunnel through said tibial aperture by drilling a longitudinal tunnel from the tibial anterior medial plateau of the tibia into said tibia and through said tibial aperture;
   e. threading an anterior cruciate ligament substitute into said femoral tunnel and into said tibial tunnel and anchoring a first end of said ligament substitute to bone leaving a free end;
   f. applying tension to said free end; and,
   g. anchoring said free end to bone under tension such that said femur and said tibia are biased together.

22. The method as recited in claim 21, wherein said steps of drilling through said femur and tibia are accomplished such that the two tunnels form an axially aligned segment.

23. The method as recited in claim 21, wherein said tibial drilling step is done such that said tibial tunnel forms an angle matching the angle of the original anterior cruciate ligament of said knee joint.

24. The method as recited in claim 21, 22, or 23, wherein said femoral drilling step is done such that said femoral tunnel forms an angle matching the angle and orientation of the original anterior cruciate ligament of said knee joint.

25. The method as recited in claim 21, 22, or 23, further comprising the steps of:
   a. prior to said step of replacing said upper portion of said tibia with a tibial component, forming said aperture in the center of said tibial component by calculating the position of a straight line traversing the longest path across the upper surface of said tibial component and forming said aperture at the center of said upper surface and intersecting said longest path traversing line.

26. A surgical kit for restoring of a mammalian knee and coupling the mammalian femur and mammalian tibia together, comprising:

a. a femoral component including a medial and lateral condyle for replacing a lower portion of a mammalian femur, said femoral component including a recess between said medial and lateral condyles defining an access way into the femur;
b. a tibial component including a surface portion adapted to slidably engage said femoral component upon rotation of said same around said femoral component for replacing an upper portion of the mammalian tibia, said tibial component including an upper surface portion that defines an aperture through said tibial component at its center;
c. at least one drill guide component adapted to guide the formation of tunnels in said femur and said tibia through said tibial aperture;
d. a ligament substitute for tensioning the femur against the tibia through said aperture, wherein said ligament substitute is adapted to be positioned such that it makes an angle approximately matching the angle of the original anterior cruciate ligament of said knee joint; and,
e. anchoring means for anchoring said ligament substitute to the femur on the exterior of the medial aspect of the posterior lateral femoral condyle and to the tibia at the exterior of tibial anterior medial plateau of the tibia.

27. A method of consuming the components of a surgical kit during total knee replacement surgery, comprising the steps of:
a. utilizing the components in a surgical kit, said kit comprising:
  i. a femoral component including a medial and lateral condyle for replacing a lower portion of a mammalian femur, said femoral component including a recess between said medial and lateral condyles defining an access way into the femur;
  ii. a tibial component including a surface portion adapted to slidably engage said femoral component upon rotation of said same around said femoral component for replacing an upper portion of the mammalian tibia, said tibial component including an upper surface portion that defines an aperture through said tibial component at its center and adapted to be canted laterally relative to said knee joint;
  iii. at least one drill guide component adapted to guide the formation of tunnels in said femur and said tibia through said tibial aperture;
  iv. an anterior cruciate ligament substitute for tensioning the femur against the tibia through said aperture, wherein said ligament substitute is adapted to approximately match the angle of the original anterior cruciate ligament relative to the medial joint line of said knee joint; and,
  v. anchoring means for anchoring said ligament substitute to the femur on the exterior of the medial aspect of the posterior lateral femoral condyle and to the tibia at the exterior of tibial anterior medial plateau of the tibia.

28. A prosthetic knee implant for connecting a mammalian femur and a mammalian tibia, comprising:
a. a femoral component positioned to replace the lower end of said femur, said femoral component shaped such that the lower end of the femur may be accessed through said femoral component;
b. a tibial component positioned to replace the upper end of said tibia, and wherein said bearing surface is shaped to cooperatively receive the lower surface of said femoral component for free rotation thereupon;
c. wherein said bearing surface defines an aperture canted to match the angle of the original anterior cruciate ligament; and,
d. an anterior cruciate ligament substitute threaded through said aperture and said femoral access way, and further adapted to be positioned to pass through tunnels formed in the femur and in the tibia, and wherein said ligament substitute forms an axially aligned segment angled to approximately match the angle of the original anterior cruciate ligament in the knee joint.

29. A prosthetic knee implant for connecting a mammalian femur and a mammalian tibia, comprising:
a. a femoral component positioned to be affixed to the femur at its lower end, said femoral component shaped such that the lower end of the femur may be accessed through said femoral component;
b. a tibial component adapted to be affixed to the tibia at its upper end, said tibial component including a bearing surface on an upper portion thereof, and wherein said bearing surface is shaped to cooperatively receive the lower surface of said femoral component for free rotation thereupon;
c. wherein said bearing surface defines an aperture positioned at its center and canted to match the angle of the original anterior cruciate ligament of said knee joint; and,
d. a ligament substitute threaded through said aperture and said femoral access way, wherein said ligament substitute is positioned such that it makes an angle approximately matching the angle of the original anterior cruciate ligament of said knee joint and is positioned such that one end can be anchored onto the tibial anterior medial plateau of the tibia and the other end can be anchored to the medial aspect of the posterior lateral femoral condyle.

* * * * *